(12) United States Patent
Hoyberg

(10) Patent No.: US 9,775,687 B1
(45) Date of Patent: Oct. 3, 2017

(54) MAGNETIC TOOTH ALIGNMENT DEVICES AND RELATED METHODS

(71) Applicant: Christian Hoyberg, El Dorado Hills, CA (US)

(72) Inventor: Christian Hoyberg, El Dorado Hills, CA (US)

(*) Notice: Subject to any disclaimer, the term of this patent is extended or adjusted under 35 U.S.C. 154(b) by 112 days.

(21) Appl. No.: 14/801,556

(22) Filed: Jul. 16, 2015

Related U.S. Application Data

(60) Provisional application No. 62/025,959, filed on Jul. 17, 2014.

(51) Int. Cl.
*A61C 7/00* (2006.01)
*A61C 7/08* (2006.01)

(52) U.S. Cl.
CPC ............ *A61C 7/006* (2013.01); *A61C 7/08* (2013.01)

(58) Field of Classification Search
CPC ....................................................... A61C 7/08
See application file for complete search history.

(56) References Cited

U.S. PATENT DOCUMENTS

| 4,396,373 | A | * | 8/1983 | Dellinger | ............... | A61C 7/006 |
| | | | | | | 433/19 |
| 7,712,468 | B2 | * | 5/2010 | Hargadon | ............... | A61F 5/566 |
| | | | | | | 128/848 |
| 9,498,302 | B1 | * | 11/2016 | Patel | ...................... | A61C 7/006 |
| 2008/0044786 | A1 | * | 2/2008 | Kalili | ....................... | A61C 7/08 |
| | | | | | | 433/6 |
| 2010/0183997 | A1 | * | 7/2010 | Darendeliler | .......... | A61C 7/006 |
| | | | | | | 433/6 |

FOREIGN PATENT DOCUMENTS

KR 200453996 Y1 * 6/2011

* cited by examiner

*Primary Examiner* — Ralph Lewis
(74) *Attorney, Agent, or Firm* — IPTechLaw

(57) ABSTRACT

A magnetic tooth alignment device includes a first magnetizable element configured to be adhered to a tooth. The magnetizable element may be a magnet, a metal, or another magnetizable material. An aligner tray is configured to partially encase a plurality of teeth and the first magnetizable element. A secondary magnet holder is configured to partially encase the aligner tray. The secondary magnet holder includes a secondary magnet configured to magnetically interact with the first magnetizable element when the secondary magnet holder is partially encasing the aligner tray. An inner wall of the aligner tray includes a cavity and the inner wall is configured to stop movement of the tooth when the first magnetizable element enters the cavity and contacts the inner wall of the aligner tray. The aligner tray in implementations couples with the plurality of teeth using only a friction fit.

20 Claims, 8 Drawing Sheets

MAGNETIC TOOTH ALIGNMENT DEVICES AND RELATED METHODS

CROSS REFERENCE TO RELATED APPLICATIONS

This document claims the benefit of the filing date of U.S. Provisional Patent Application No. 62/025,959, entitled "Magnetic Tooth Alignment Devices and Related Methods," naming as first inventor Christian Hoybjerg, which was filed on Jul. 17, 2014, the disclosure of which is hereby incorporated entirely herein by reference.

BACKGROUND

1. Technical Field

Aspects of this document relate generally to orthodontic devices. Specific implementations relate to orthodontic alignment devices.

2. Background Art

Orthodontics is a branch of dentistry dealing with alignment of the teeth and/or jaws of a patient. Conventional devices used for tooth and/or jaw alignment include traditional metal dental braces adhered to the teeth or rigid plastic trays that are not permanently affixed to the teeth. After the desired alignment has been achieved using conventional devices, retainers are often used to prevent the teeth/jaw from returning to pre-alignment positions.

SUMMARY

Implementations of magnetic tooth alignment devices may include: a first magnetizable element configured to be adhered to a tooth of a patient; an aligner tray configured to at least partially encase a plurality of teeth of the patient and the first magnetizable element, and; a secondary magnet holder configured to at least partially encase the aligner tray, the secondary magnet holder including a secondary magnet configured to magnetically interact with the first magnetizable element when the secondary magnet holder is partially encasing the aligner tray.

Implementations of magnetic tooth alignment devices may include one, all, or any of the following:

The aligner tray may be formed of a polymer.

The aligner tray may be transparent.

The aligner tray may include no magnets.

The aligner tray may be configured to couple with the plurality of teeth of the patient using only a friction fit.

The aligner tray may be configured to fully encase the plurality of teeth of the patient and to fully encase the first magnetizable element.

The aligner tray may include a protrusion defining a cavity between the aligner tray and the first magnetizable element.

The secondary magnet holder may be shaped substantially similar to the aligner tray.

The secondary magnet holder may be configured to couple with the aligner tray using only a friction fit.

The first magnetizable element may be formed of one of a powdered magnetic material mixed with an adhesive and a cement magnetic material.

An inner wall of the aligner tray may be configured to stop movement of the tooth when the first magnetizable element contacts the inner wall of the aligner tray.

Implementations of magnetic tooth alignment devices may include: a first magnetizable element configured to be adhered to a tooth of a patient; an aligner tray configured to at least partially encase a plurality of teeth of the patient, the aligner tray including a protrusion defining a cavity between the aligner tray and the first magnetizable element, the aligner tray including no magnets; and; a secondary magnet holder configured to at least partially encase the aligner tray, the secondary magnet holder including a secondary magnet configured to magnetically interact with the first magnetizable element when the secondary magnet holder is partially encasing the aligner tray.

Implementations of magnetic tooth alignment devices may include one, all, or any of the following:

The secondary magnet holder may be configured to couple with the aligner tray using only a friction fit.

The aligner tray may be formed of a polymer.

The aligner tray may be transparent.

The secondary magnet holder may have a shape substantially similar to the aligner tray.

The secondary magnet may have a dental arch shape.

Implementations of magnetic tooth alignment devices may include: a first magnet configured to be adhered to a tooth of a patient; an aligner tray configured to at least partially encase a plurality of teeth of the patient and the first magnet, and; a secondary magnet holder configured to at least partially encase the aligner tray, the secondary magnet holder including a secondary magnet configured to magnetically interact with the first magnet when the secondary magnet holder is partially encasing the aligner tray.

Implementations of magnetic tooth alignment devices may include one, all, or any of the following:

The aligner tray may include no magnets.

The secondary magnet holder may have a shape substantially similar to the aligner tray.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

Implementations will hereinafter be described in conjunction with the appended drawings, where like designations denote like elements, and.

DESCRIPTION

This disclosure, its aspects and implementations, are not limited to the specific components, assembly procedures or method elements disclosed herein. Many additional components, assembly procedures and/or method elements known in the art consistent with the intended magnetic tooth alignment devices and related methods will become apparent for use with particular implementations from this disclosure. Accordingly, for example, although particular implementations are disclosed, such implementations and implementing components may comprise any shape, size, style, type, model, version, measurement, concentration, material, quantity, method element, step, and/or the like as is known in the art for such magnetic tooth alignment devices and related methods, and implementing components and methods, consistent with the intended operation and methods.

Figure 1:
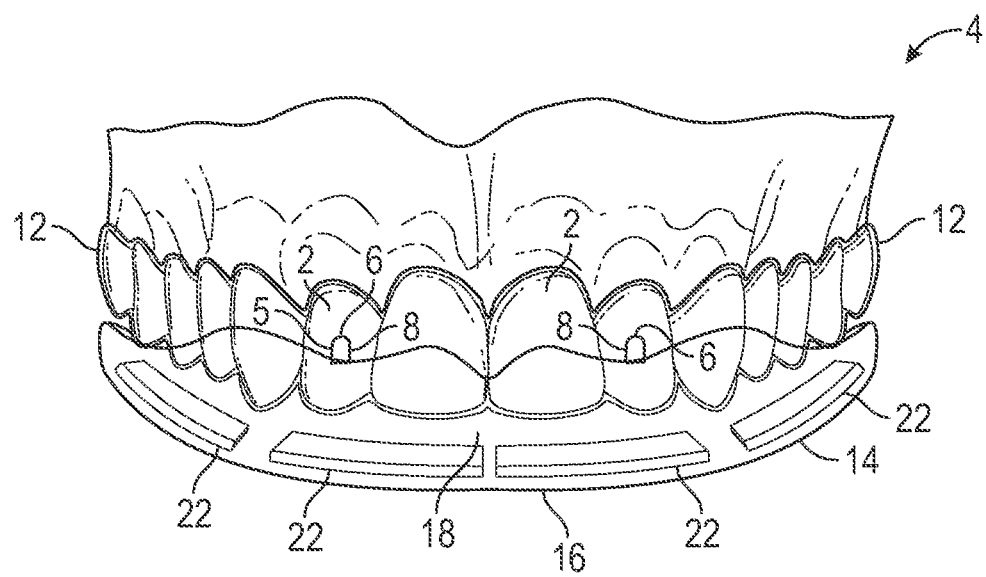
FIG. 1 is a front view of an implementation of a magnetic tooth alignment device.
Figure 2:
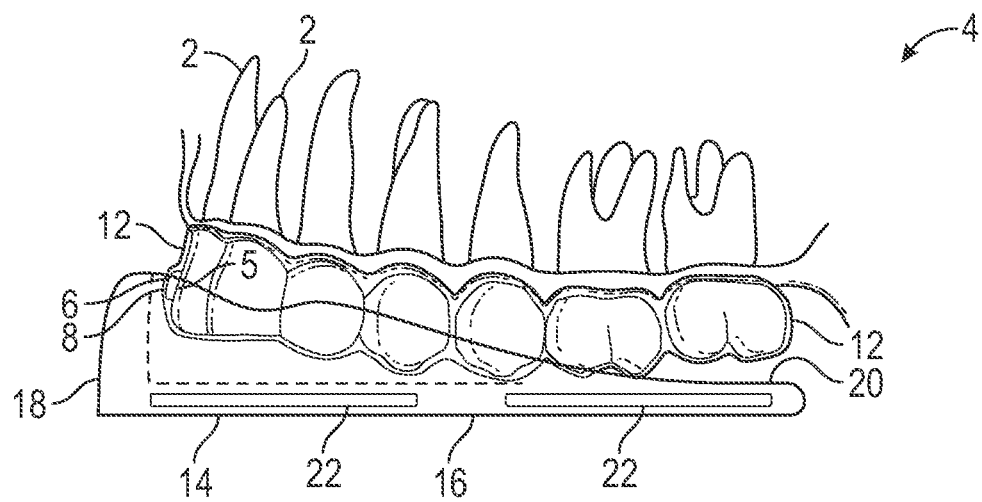
FIG. 2 is a side view of the magnetic tooth alignment device of FIG. 1.
Figure 3:
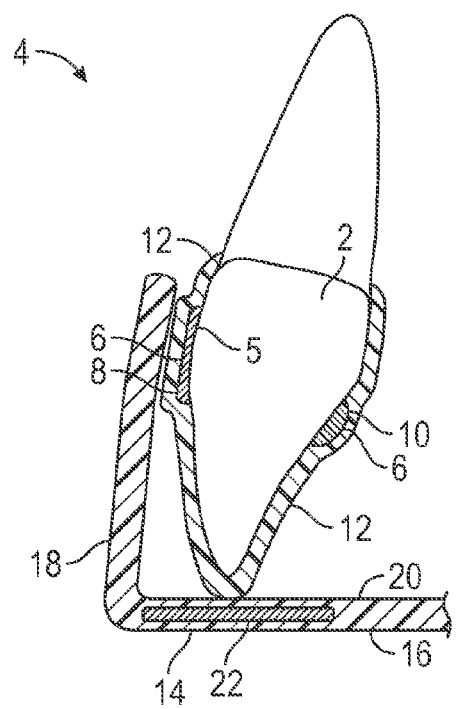
FIG. 3 is a side cross-section view of an implementation of a magnetic tooth alignment device.
Figure 4:
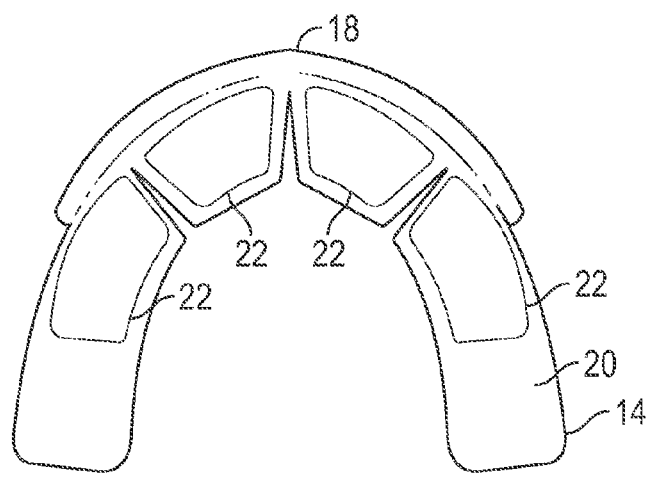
FIG. 4 is a top see-through view of an implementation of a secondary magnet holder of a magnetic tooth alignment device.
Figure 5:
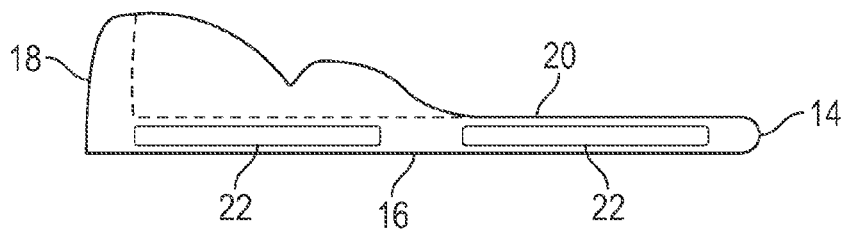
FIG. 5 is a side see-through view of the secondary magnet holder of FIG. 4.

Referring now to FIG. 1, a front see-through view of an implementation of a magnetic tooth alignment device (device) 4 is shown coupled to an upper row of teeth 2. FIG. 2 shows a side see-through view of the device 4 coupled to an upper row of teeth, with the roots of the teeth visible. FIG. 3 is a side cross-section view of the device 4 coupled to an upper row of teeth. FIG. 4 is a top view of an implementation of a secondary magnet holder 14 of device 4, showing the top 20 of the secondary magnet holder. FIG. 5 is a side view of the secondary magnet holder 14.

Referring now to FIG. 1, in various implementations, a magnetic tooth alignment device 4 includes a magnetizable element 5 coupled to a tooth 2. The magnetizable element 5 is an element which may be attracted by a magnet. As such, the magnetizable element could be formed of a solid metal, or metal powder mixed in a binder, and so forth. In other implementations the magnetizable element could be, itself, a magnet, such as primary magnet 6 shown in FIG. 1. In implementations in which the magnetizable element is a magnet it is capable of being not only attracted by another magnet but also repelled by another magnet depending on how the poles of the magnets are oriented relative to each other.

An aligner tray 12 is couples to/over/partially over one or more teeth and is provides a stopping point for movement of the one or more teeth, and a secondary magnet holder 14 couples to the aligner tray. The secondary magnet holder has one or more secondary magnets 22 therein (and/or thereon).

The primary magnets 6 may be tooth-colored or may have some other color that allows them to blend in well with the color of the teeth. For instance the outer color of the primary magnets 6 may be, in various implementations, selected from at least the shades A1, A2, A3, clear or transparent. The primary magnets 6 may include a magnetic portion and a surface covering the magnetic portion. In such implementations, the surface covering may be a composite material and/or may be tooth colored to help the primary magnets 6 visibly blend in with the appearance of the teeth.

In FIG. 1 the primary magnets are shown on the front (buccal side) of the teeth, while FIG. 3 illustrates how the primary magnets 6 may also be placed on the back (lingual) side of the teeth. The primary magnets 6 may be placed on the teeth with a glue, cement, or other material capable of bonding/coupling the magnet to the tooth 2. Depending upon the material used, the primary magnets 6 may later be removed by applying a solvent to the glue, cement, or other bonding/coupling material. Although the primary magnets 6 are only shown on the front (buccal) and back (lingual) faces of the teeth, they may also be placed or attached to any other exposed surface of a tooth 2. A magnetic tooth alignment device may include any number of primary magnets on any number of teeth. For instance, in some cases there may be only one tooth that needs movement and, in that case, there may be only one primary magnet, or there may be multiple magnets at different locations on that one tooth, to assist in movement of that tooth over time in a desired direction(s) during orthodontic treatment. For example, in FIG. 3 there is shown a first primary magnet 8 on the front (buccal) side of the tooth 2 and a second primary magnet 10 shown on the back (lingual) side of the tooth 2. In other cases there may be multiple teeth that need movement. Accordingly, in various implementations there may be a plurality of teeth to which a plurality of primary magnets are attached.

In various device implementations, any type of magnetic material may be used for the primary magnets, though in some implementations rare-earth element magnets may be used in order to develop sufficient magnetic forces while using appropriately-sized magnets. By non-limiting example, the primary magnets in implementations may include neodymium. In other implementations the primary magnets may be formed of other magnetic materials, including magnetic alloys, ferromagnetic alloys, and the like.

The primary magnets may take many cross sectional and three dimensional shapes. Some shapes may be anatomically designed to match specific teeth. In some implementations of magnetic tooth alignment devices the primary magnets may all have the same, or substantially the same shape, which may be an average shape designed to work with the majority of tooth structures.

Referring to FIGS. 1-5, the magnetic tooth alignment device also includes an aligner tray 12. After the magnetizable elements, such as primary magnets, are glued, cemented, bonded, coupled, or otherwise adhered to the teeth, the aligner tray 12 is coupled over the teeth or, in other words, may partially encase/enclose, or fully encase/enclose, the teeth. In the figures the aligner tray 12 fully encases the teeth, but the practitioner of ordinary skill in the art may envision versions in which the teeth are not fully encased. The aligner tray 12 may be formed of a clear polymer, though it may also be formed of a non-polymeric material, a composite material, and/or an opaque material. The aligner tray 12 is selectively attached to the teeth with a friction fit and, accordingly, may be slid off or on the teeth as desired by a user by overcoming the friction between the tray and the teeth. The aligner tray 12 will cover or surround, at least partially (and in some implementations completely or substantially completely) at least one tooth that is to be moved (and in many cases several or many teeth that are to be moved). The structure of the aligner tray 12 provides the stopping point for tooth movement during magnetic orthodontic alignment and accordingly each single-tooth portion of the aligner tray 12 is configured so that when the tooth abuts/contacts it (or when the magnetizable element attached to the tooth abuts/contacts it) the tooth will be in the desired position for that stage of orthodontic treatment. Thus the aligner tray 12 is sufficiently rigid, and the magnetic forces of the primary and secondary magnets of such a magnitude, that when the teeth reach the aligner tray 12 they do not, or substantially do not, distort or move the tray—but instead stop further movement upon contacting the surface of the tray.

For example, a primary magnet may be attached to the buccal side of a tooth and an attractive opposite poled secondary magnet may be used to draw that tooth in the buccal direction, or in other words towards the inner buccal sidewall of the aligner tray. As another example, a primary magnet could be attached to the buccal side of a tooth and aligned so that similar poles of the primary magnet and secondary magnet are near one another to provide a repulsive force so that the tooth is pushed back towards the lingual side of the aligner tray. Thus, the primary and secondary magnets may utilize magnetic attraction and/or repulsion through opposite and same magnetic poles in order to achieve the desired magnetic force and direction though, as described above, when only attraction is needed the magnetizable element need not be a magnet. Additionally, any type of orthodontic tooth movement may be accomplished using implementations of a magnetic tooth alignment device including, but not limited to, extrusion, bodily movement, intrusion, expansion, and the like.

During the process of orthodontic treatment using magnetic tooth alignment devices, several differently shaped aligner trays may be used at different stages so as to ensure incremental movement of the teeth at a desired rate. Thus when one or more teeth have reached a location of abutting a particular/first aligner tray, that first aligner tray may be switched out with another/second aligner tray to provide new boundaries for the teeth to reach as they move under the magnetic forces.

Referring still to FIGS. 1-5, the magnetic tooth alignment device includes a secondary magnet holder 14 including one or more secondary magnets 22. The secondary magnets 22 may be placed in different locations within or on the secondary magnet holder 14. In the implementations shown in FIGS. 1-5 there are four secondary magnets 22 and they are each encased within a bottom section of the secondary magnet holder 14, and the magnets are generally shaped and positioned to align with a dental arch. In other implementations, the secondary magnet 22 may be a single magnet shaped and positioned to align with a specific location along the dental arch. Referring to FIG. 3, the secondary magnet holder 14 could, alternatively or additionally to having the secondary magnet(s) housed in the bottom 16 of the secondary magnet holder, have one or more secondary magnets in or on the front 18 of the secondary magnet holder.

The secondary magnet holder 14 is configured to selectively couple at least partially, and in some cases fully or substantially fully, over the aligner tray 12. In various implementations, this coupling is accomplished with a friction fit between the secondary magnet holder 14 and the aligner tray 12, this friction fit being able to be overcome manually by a user. In other implementations the secondary magnet holder 14 is configured to selectively couple over the aligner tray 12 through a clip-on mechanism which also may be overcome through the manual force of a user to remove the secondary magnet holder. In other implementations, the coupling may take place at least in part through the magnetic forces between the primary and secondary magnets.

Referring to FIG. 3, a number of tooth movement operations may be accomplished by altering sizes, magnetic strengths, locations and polarities of the primary and secondary magnets of a magnetic tooth alignment device. By non-limiting example, in the implementation shown in FIG. 3, the first primary magnet 8 could be attracted to the secondary magnet 22 and the second primary magnet 10 could also be attracted to the secondary magnet 22 and this could result in pulling the entire tooth downwards towards the secondary magnet 22 (resulting in extrusion of the tooth 2). However, the first primary magnet 8 could be attracted to the secondary magnet 22 and the second primary magnet 10 could be repelled by the secondary magnet 22 and this could result in a rotation of the longest length of the tooth so that the bottom of the tooth is moved farther away from the front of the aligner tray (resulting in tipping of the tooth 2). The opposite rotation could be accomplished by reversing the polarities of the first and second primary magnets 8, 10 (or only that of the secondary magnet 22). Both the first and second primary magnets 8, 10 could have a polarity such that they are repelled by the secondary magnet 22 and this could tend to push the tooth upwards away from the secondary magnet (resulting in intrusion of the tooth 2) or to otherwise prevent or hinder downward movement of the tooth during the orthodontic treatment. The size and the strength of the magnets may be altered, as well, to increase or decrease the rate at which movement occurs, or to alter the forces on the teeth to achieve the desired movement, and so forth. As there may be many possible variations on the size, strength, polarity, and position of the various magnets of a magnetic tooth alignment device, these variables may be chosen so as to accomplish the desired tooth movement.

During orthodontic treatment when the secondary magnet holder 14 is coupled to the aligner tray 12, the secondary magnet(s) 22 generally stay fixed while each primary magnet 6 moves either towards or away from a secondary magnet 22 to effectuate movement of the teeth to which the primary magnets are attached. Once the full desired movement of the teeth has been accomplished, the patient discontinues using the secondary magnet holder and the aligner tray. The primary magnets are removed from the teeth, and a retainer is fabricated and/or used to retain the teeth in their final, proper aligned positions. In implementations the retainer may be clear and/or may otherwise be similar in some respects to the aligner tray, and in implementations may be, by non-limiting example, a vacuum-formed retainer formed using a polymer sold under the trade name ESSIX by Dentsply International Inc. of York, Pa., a thermo-formed retainer formed using a polymer sold under the trade name ZENDURA by Bay Materials, LLC of Menlo Park, Calif., a fixed retainer, a Hawley retainer, or the like. In various implementations, the aligner tray 12 may also be formed of the ESSIX or ZENDURA materials.

The secondary magnet holder 14 may be re-utilized in cases where the teeth begin to relapse. In the case of relapse one or more primary magnets 6 may be coupled to the tooth 2 or teeth again and windows may be cut in the retainer (if the retainer would otherwise interfere with the primary magnet(s) to allow the magnet(s) to pass therethrough, or a retainer with protrusions/cavities to receive the magnets could be used (similar to aligner tray 34 discussed below), and the secondary magnet holder 14 may be utilized again. In such an instance the retainer itself acts as an aligner tray.

In some implementations, the secondary magnets 22 will be completely or substantially encased within the secondary magnet holder. In other implementations they may be attached to the outside of the secondary magnet holder or only partially encased therein. The secondary magnet holder may be formed of a polymer material, which may be any of those disclosed in this document, though in other implementations it could be formed of some other material, such as a composite material. In some versions the secondary magnets may be removable from the secondary magnet holder.

In implementations the aligner tray 12 itself could include magnets, or the secondary magnets could be attached directly to the aligner tray. In some versions of a magnetic tooth alignment device a chewable element may be used. By non-limiting example, in some implementations the secondary magnet holder may not attach to the aligner tray but may comprise a chewable element that includes a secondary magnet therein, and the magnetic forces between the primary magnets and secondary magnet(s) operate while the patient is chewing on the secondary magnet holder. The secondary magnet holder in such implementations may be formed of a rubbery polymer or a rubbery composite material. The secondary magnet holder in such instances could be an aligner tray seater sold under the trade name CHEWIES by Dentsply Raintree Essix of Sarasota, Fla., with a secondary magnet placed therein (and/or retained therein such as with a glue or cement). In implementations the secondary magnet holder may have a shape somewhat different than CHEWIES aligner tray seaters such as, by non-limiting example, a shape of a block, cube or right rectangular cuboid having a cavity therein receiving the secondary magnet.

A number of orthodontic treatment method implementations may be employed with the implementations of magnetic tooth alignment devices disclosed in this document. In a first method, the primary magnets, secondary magnet(s) and secondary magnet holder are provided. A dental practitioner (such as an orthodontist or an assistant) attaches the primary magnets to the teeth and then takes an impression of the teeth with primary magnets coupled thereon. The impression is used to form an aligner tray with proper dimensions to begin magnetic orthodontic treatment. This method may result in fewer refinements needing to be made to aligner trays, since the trays are custom built for the patient, which may result in less treatment time for the dental practitioner and patient, lower cost for the patient and/or a lower cost or higher profit for the dental practitioner. It may also result in a lower cost or decreased time for the party that provides the alignment tray since there may be fewer revisions to each tray.

In a second method of orthodontic treatment, a dental practitioner attaches the primary magnets to the teeth and then takes an impression (such as, by non-limiting example, a polyvinyl siloxane (PVS) impression). This impression is used to pour a model with dental model stone. The teeth of the dental model stone are manually placed in their desired locations and then used in the aligner tray manufacturing process to create an aligner tray. The resulting aligner tray is worn by the patient, along with the secondary magnet holder which has one or more secondary magnets, until the desired movements of the teeth are accomplished (which may involve the use of other incrementally changing aligner trays as discussed herein). Once the teeth have reached their desired positions, the primary magnets may be removed from the teeth and a retainer may be formed for retention of the teeth. If the teeth relapse, a dental practitioner can reattach the primary magnets as needed and, if necessary, cut windows through the retainer, so that the patient may wear the secondary magnet holder on top of the retainer to help move the teeth back to their proper positions.

In a third method of use, a dental practitioner will attach the primary magnets to the teeth. An impression will then be taken such as, by non-limiting example, a polyvinyl siloxane (PVS) impression. A three-dimensional (3-D) scan of the impression will be taken and data related thereto will be uploaded to a server. A computer software program in communication with the server will analyze the 3-D data and output one or more of the following: (1) data used to form the first, or multiple, or all of the aligner trays (including in some implementations the final retainer) that will be used during orthodontic treatment of the teeth; (2) data used to determine one or more of size, strength, location, and number of primary magnets on the teeth of the patient; (3) data used to determine which of a number of secondary magnet holders and secondary magnets to use; (4) an estimation of tooth movement during orthodontic treatment, and; (5) a calculation of the force and/or time needed to perform each incremental, or the full, tooth movement for each tooth to be moved. In implementations this process may be repeated each time the new aligner tray is to be replaced, and in such implementations the computer software program may utilize the some or all prior 3-D data in conjunction with the new 3-D data collected during the treatment process to perform its functions.

In various implementations, the computer software program may calculate attractive forces between magnets (or between magnets and magnetizable elements). In implementations the computer software program may calculate repelling forces between magnets. In implementations the computer software program may utilize the following equation in determining the force between two magnets by estimating the force between two magnetized surfaces, where A is the area of each surface measured in square meters, H is their magnetizing field measured in Amps/meter, $\mu_0$ is the permeability constant which equals $4\pi 10^{-7}$ Tm/A (Tesla meters per amp) and B is the magnetic flux density measured in Teslas.

$$F = \frac{\mu_0 H^2 A}{2} = \frac{B^2 A}{2\mu_0}$$

As this equation is more valid for cases in which the effect of fringing is negligible and the volume of the gap between magnets is much smaller than the dimensions of the magnetized material, in implementations in which fringing is not negligible and/or the gap is not much smaller than the dimensions of the magnetized material, other equations to correct for such effects may be utilized by the computer software program.

The practitioner of ordinary skill in the art will readily understand that the computer software program may utilize a multitude of equations, values, inputs, logic, and the like to calculate forces that will be exerted on teeth, which in some cases may be estimated by calculating the force between two isolated magnets, such as one primary magnet and one secondary magnet, or which in other cases may be estimated by calculating the cumulative force on each primary magnet taking into account all other primary and secondary magnets of the magnetic tooth alignment device that exert a non-negligible force thereon.

In various implementations, a magnetic tooth alignment device may also cause movement of the teeth through other than magnetic forces. For instance, the aligner tray may also place mechanical pressure on one or more teeth to move them, by contacting the teeth directly, in addition to/in combination with the magnetic forces that are exerted on the teeth due to the magnets. In various implementations, the magnetic tooth alignment device could be used in conjunction with other types of tooth movement devices (braces, etc.) to move the teeth to their desired locations.

In particular implementations, the magnetic tooth alignment device when used for extrusion may provide any of the following: light, constant forces such as, by non-limiting example, 15 g (or about 15 g) for anterior teeth and 50 g (or about 50 g) for posterior teeth; a steady, slow rate for tooth movement such as, by non-limiting example, no more than about 2.0 mm per month, and/or; a retention and stabilization period of no less than one month for every month of active extrusion.

In some implementations the magnetic tooth alignment device may be used for crowns that have broken off and need crown lengthening. In general such crowns do not have enough tooth structure for brackets, so the only option for treatment has been a crown lengthening procedure. This procedure requires cutting gum away from bone and then grinding bone away from tooth until adequate tooth structure is present to cement a crown. As an alternative to this procedure, the magnetic tooth alignment device may be utilized, with a primary magnet placed on the remaining tooth structure and the secondary magnet used to extrude the tooth to an ideal length without a need for surgical crown lengthening.

In various implementations, the secondary magnet holder may be formed by incorporating a magnet into or on an athletic mouth guard or may otherwise have the same shape, or a shape similar to an athletic mouth guard, such as are used in contact sports like football, boxing, etc.

In implementations of primary and secondary magnets that include neodymium the amount of neodymium may vary based on the shape of the magnet. Some implementations of primary and secondary magnets will consist 100% of an alloy of neodymium, iron and boron in the $Nd_2Fe_{14}B$ tetragonal crystalline structure. The primary magnets 6 in various implementations will have a size of, or of about, 1 mm×2 mm with a thickness of, or of about, 0.5 mm to 0.75 mm. The primary magnets may have a size of, or of about, 1 mm×2 mm×0.75 mm, and may have a tapered shape. The primary magnets may have a size of, or of about, 1 mm in height, 2 mm in width, and 0.75 mm thick. The thickness of the primary magnet may be, or may be about, 0.5 mm at the gingival aspect of the tooth and increase to, or to about, 0.75 mm thickness at the incisal edge of the tooth. A polyurethane coating may be placed over the primary and secondary magnets to make them biocompatible. The polyurethane coating may be, or may be about, 0.001 mm thick, coating the entire magnet. A second coating may be placed over the polyurethane coating, which may be a composite/resin of, or of about, 0.2 mm thick, on the buccal surface, to create the tooth colored coating, and may have the appearance of an enamel coating. Carbon fiber coatings may be used in some implementations on the primary and/or secondary magnets to provide the tooth colored coating, which may be thinner than 0.2 mm thick.

In various implementations, the secondary magnet holder 14 may be formed of the aforementioned ESSIX material. The secondary magnet holder may be formed of any of many different polymeric materials commonly used to form athletic mouth guards or mouthpieces which may be softer and allow for a more cushioned bite compared with the ESSIX material. Various other polymer materials may be used to form the secondary magnet holder. In implementations the secondary magnet holder may have an arched shape and be a one-size-fits-all form. The segmented nature of the secondary magnet holder shown in FIGS. 1-5 may facilitate the ability of the secondary magnet holder to have this one-size-fits-all functionality. In some cases the secondary magnet(s) will be held in place within, or attached to, the secondary magnet holder at least partly from pressure on or from the segments. This pressure may comprise a transverse force or a minor squeeze which may be not enough to cause discomfort or tooth movement. Magnetic molar attachments may be placed on the buccal surface of upper molars, which in some cases may be rectangular and may have dimensions of, or of about, 1 mm×2 mm. The rectangular magnetic molar attachments may aid in holding the secondary magnet holder in the mouth, the secondary magnet and/or other magnet(s) of the secondary magnet holder being attracted thereto. The aligner tray and the magnetic molar attachments may form a convexity (convex shape) to which the secondary magnetic holder couples.

The magnetic tooth alignment device may have the following attributes: greater rate of tooth movement than is possible with conventional clear aligners alone; more full tooth movement (closer to desired end-positioning) than is possible with conventional clear aligners alone; less overstressing of teeth than occurs with wire movement of teeth (using braces)—this may reduce root resorption and unneeded tooth movement (tipping); increased ability for extrusion movement of teeth over conventional clear aligners; greater success rate for tooth extrusion (compared to about 29% success rate for conventional clear aligners); more predictable movement of teeth during treatment than conventional clear aligners and braces; more types of movement of teeth than are possible with conventional aligners alone; no need to use overlay wires to avoid tipping of teeth adjacent to teeth that are intentionally being moved; increased ability for tooth expansion compared to conventional aligners, which are generally incapable of providing the forces needed for proper expansion, and more predictable expansion, without having to change the clear aligner material (i.e., while using the same material for the aligner tray as is used for conventional clear aligners); allowing placement of magnets on the lingual surfaces of dentition, thus providing a non-visible alternative to braces; less bulky attachments in general as compared with braces and conventional tooth-movement technology, and; the ability for expose and bond procedures—conventional clear aligner treatment does not involve expose and bond procedures, thus requiring a patient to turn to surgery or braces as the only options for such treatment—with the ability to place a primary magnet on an exposed tooth the secondary magnet may put the necessary pull on the tooth to extrude it out of bone and gum.

In implementations the primary magnets 6 and/or secondary magnets 22 may be formed of a magnetic resin and/or a composite material having magnetic filings or a magnetic powder mixed with a cement or glue—such as by non-limiting example a clear tetracyanoethylene magnetic powder. The primary magnets and secondary magnets may have coatings to increase their biocompatibility and/or to prevent corrosion or other effects on the magnet. The primary magnets and/or secondary magnets may be formed of a magnetic material added to a cement, resin or adhesive which is then formed into the desired shape.

The primary and secondary magnets may, in implementations, be fabricated by Dexter Magnetics of Elk Grove Village, Ill. Coatings placed on the primary and/or secondary magnets may, in implementations, be provided or applied by Paratronix, Inc. of Attleboro, Mass.

Various details disclosed herein with regards to primary magnets, such as size, shape, manufacturing techniques, color, coatings, placement on a tooth, etc., may also apply to magnetizable elements 5 that are not actually magnets.

Although the magnetizable element 5 in FIGS. 1-5 is represented as a magnet, it is to be understood that the magnetizable element in any of these implementations may be a non-magnet instead, such as a metal that is attracted to the secondary magnet 22 by virtue of its being a magnetizable metal (stainless steel, by non-limiting example).

Figure 6:
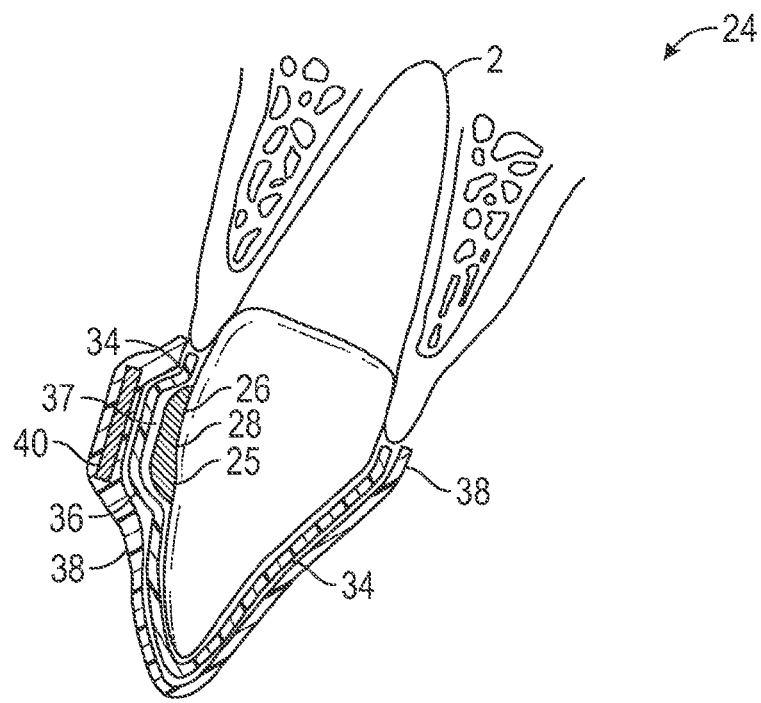
FIG. 6 is a side cross-section view of an implementation of a magnetic tooth alignment device.
Figure 7:
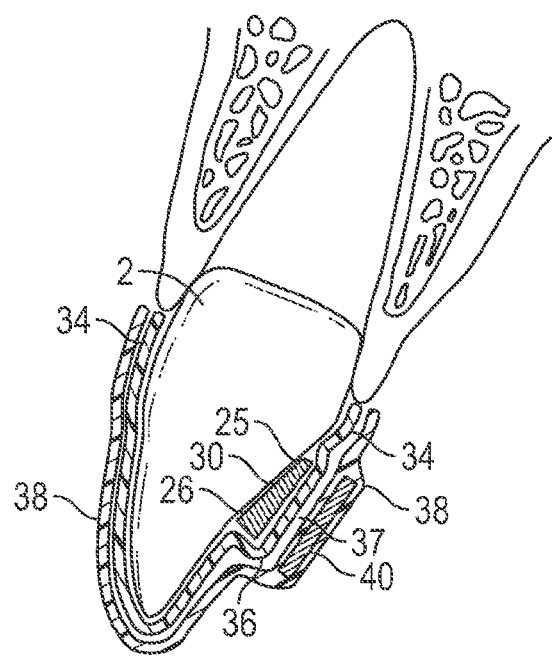
FIG. 7 is a side cross-section view of an implementation of a magnetic tooth alignment device.
Figure 15:
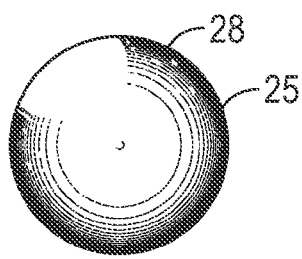
FIG. 15 is a top view of an implementation of a first primary magnet of a magnetic tooth alignment device.
Figure 16:
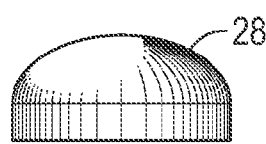
FIG. 16 is a side view of the first primary magnet of FIG. 15.
Figure 17:
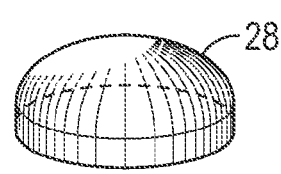
FIG. 17 is a perspective view of the first primary magnet of FIG. 15.
Figure 18:
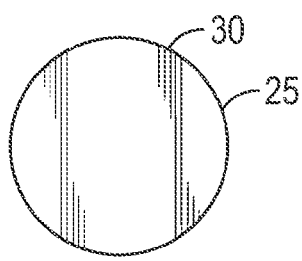
FIG. 18 is a top view of an implementation of a second primary magnet of a magnetic tooth alignment device.
Figure 19:
FIG. 19 is a side view of the second primary magnet of FIG. 18.
Figure 20:
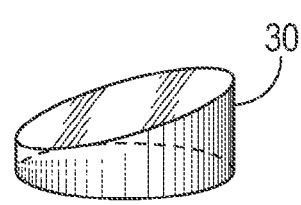
FIG. 20 is a perspective view of the second primary magnet of FIG. 18.
Figure 21:
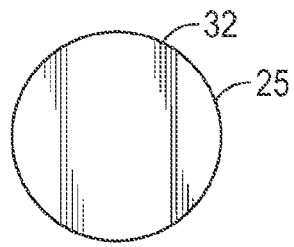
FIG. 21 is a top view of an implementation of a third primary magnet of a magnetic tooth alignment device.
Figure 22:
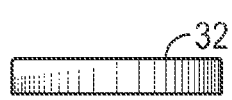
FIG. 22 is a side view of the third primary magnet of FIG. 21.
Figure 23:
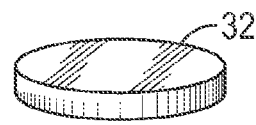
FIG. 23 is a perspective view of the third primary magnet of FIG. 21.

Referring now to FIG. 6, in implementations a magnetic tooth alignment device (device) 24 includes a magnetizable element 25 attached to a tooth 2. The magnetizable element 25 in implementations may be formed of a magnet, such as primary magnet 26, though in other implementations it may be a non-magnetic element, such as a metal. The device 24 shown in FIG. 6 shows a tooth 2 with a magnetizable element (in this case first primary magnet 28) on the front (buccal) side of the tooth and the device 24 shown in FIG. 7 shows a tooth with a magnetizable element (in this case second primary magnet 30) on the back (lingual) side of the tooth. The shapes of first primary magnet 28 and second primary magnet 30 are shown in greater detail in FIGS. 15-20. FIGS. 15-17 show top, side, and perspective views, respectively, of first primary magnet 28. FIGS. 18-20 show top, side, and perspective views, respectively, of second primary magnet 30. A third primary magnet 32, having a cylindrical shape, is shown in FIGS. 21-23. FIGS. 21-23 show top, side, and perspective views, respectively, of third primary magnet 32.

Although the first primary magnet 28 is shown on the front (buccal) side of the tooth and the second primary magnet 30 is shown on the back (lingual) side, in other implementations all of the magnetizable elements could have the shape of one or the other examples given in FIGS. 15-23, or any other shape. For example all magnetizable elements, whether on the front, back, side, or bottom of the tooth, could have the shape of the first primary magnet, or the second primary magnet, or the third primary magnet. Likewise, magnetizable elements having the shape of the first primary magnet could be located on the lingual side of the tooth (or on the sides), and magnetizable elements having the shape of the second primary magnet could be located on the buccal side of the tooth, or on the sides, etc. The user (dentist or other professional applying the magnetizable elements) may choose which shapes/sizes to use in each scenario, or a computer program as previously described may make such a determination. As shown in FIGS. 18-20, the shape of the second primary magnet 30 is the shape of a cylinder with one of its bases titled at an angle. Other shapes could be used than those described herein for any of the magnetizable elements and, indeed, custom shapes and molded shapes could be used to conform to a tooth so as to more easily blend in to the appearance of the tooth.

In implementations in which the magnetizable elements 25 are not magnets, they may be formed of stainless steel. In implementations in which a powder is used mixed in a binder one or more magnetic powders or salts may be used, such as salts of various first row transition metals, cyano salts, and the like. In implementations in which the magnetizable elements 25 are formed of steel they may be 17-4 stainless steel which may be purchased in a rod and machined to the proper shape and size. A stainless steel magnetizable element may have the same shape as the first primary magnet 28, which includes a half-sphere having a radius of, or of about, 1 mm. When viewed from the side as seen in FIG. 16 the half-sphere portion thus has a height of 1 mm and a diameter of 2 mm. The shape shown in FIGS. 15-16 includes the shape of a half-sphere atop the shape of a cylinder, but in other implementations a magnetizable element could have simply the shape of a half-sphere without the cylindrical portion.

When a cylindrical shape is used, as in FIGS. 21-23, the shapes may have a thickness (height in FIG. 22) of 1-2 mm, or about 1-2 mm, with a diameter of, or of about, 2 mm. When the magnetizable elements are formed of a non-magnetic material, such as steel, the magnetizable elements will not attract or repel one another. This may in some cases be advantageous because, in the event that a plurality of magnetizable elements are swallowed, there will be no magnetic attraction or repulsion of the magnetizable elements in the digestive tract of the patient. Additionally, removing magnetic interactions between magnetizable elements on neighboring teeth may reduce unwanted forces between teeth and may make modelling the movement of the teeth, with software as described above, simpler.

Various white or tooth-colored coatings may be applied to the magnetizable elements to make them blend in better. In implementations the white or tooth-colored coatings may be coatings sold and/or distributed and/or applied by Liquipel LLC of Santa Ana, Calif. Another hypoallergenic coating may be applied under or over this colored coating, and may be sold and/or distributed and/or applied under the trade name PARALYENE by Jaro Corp. of Ipswich, Mass. or Paratronix Inc. of Attleboro, Mass. PARALYENE coated magnets have been used in human studies. The coatings may be, or may be about, 0.001 mm thick, and may coat the entire surface of the magnetizable element.

FIGS. 6 and 7 both show an aligner tray 34 that is custom shaped with a protrusion 36 that forms or defines a cavity 37 between the aligner tray and the magnetizable element. The secondary magnet holder 38 shown in FIGS. 6-7 has substantially the same shape as the aligner tray and clips over the aligner tray to stay on place using only a friction fit or, in some implementations, a friction fit assisted by the magnetic attraction of the secondary magnet(s) 40 towards the magnetizable element(s) 25. In cases wherein the magnetizable element 25 is attracted towards the secondary magnet 40, the magnetizable element 25 is allowed some movement within the cavity until it abuts the inner wall of the aligner tray 34, at which point the movement stops and a new aligner tray and/or secondary magnet holder may be utilized to allow and/or effect further movement. As described above with respect to device 4, the use of device 24 may include the use of a series of aligner trays and/or secondary magnet holders, a series of positions and placements of magnetizable elements, and various of these may be computer simulated or generated using software that models the movement of the teeth based on magnetic and other forces over time.

Figure 24:
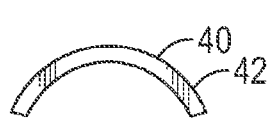
FIG. 24 is a top view of an implementation of a secondary magnet of a magnetic tooth alignment device.
Figure 25:
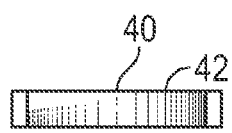
FIG. 25 is a side view of the secondary magnet of FIG. 24.
Figure 26:
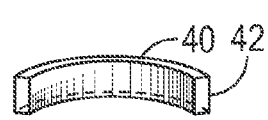
FIG. 26 is a perspective view of the secondary magnet of FIG. 24.
Figure 27:
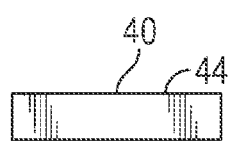
FIG. 27 is a top view of an implementation of a secondary magnet of a magnetic tooth alignment device.
Figure 28:
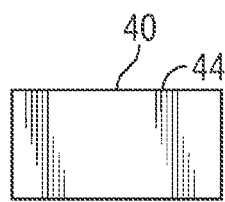
FIG. 28 is a side view of the secondary magnet of FIG. 27.
Figure 29:
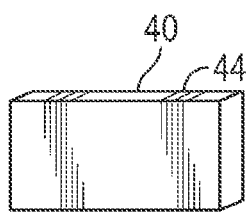
FIG. 29 is a perspective view of the secondary magnet of FIG. 27.

A first shape 42 for a secondary magnet 40 is shown in FIGS. 24-26, and a second shape 44 for a secondary magnet is shown in FIGS. 27-28. FIGS. 24-26 show top, side, and perspective views, respectively, of first shape 42. This is an arcuate shape or a dental arch shape 42. As can be seen in FIGS. 25-26 the height is greater than the thickness in some implementations and the arc spans close to a 90 degree arc. Other versions may have other dimensions. In various implementations, an arch shaped secondary magnet may have dimensions of, or of about, 1⅛ inch outer radius, 1 inch inner radius, ⅛ inch height, ⅛ inch thickness, and a 45 degree arc. FIGS. 27-29 show top, side, and perspective views, respectively, of a second shape 44 for a secondary magnet, which has the shape of a right rectangular cuboid. Other shapes may be used for the secondary magnets, and indeed any custom shape could be used as desired by a user or as generated by a computer software program for proper tooth movement.

The secondary magnet(s) 40 may in implementations be formed of neodymium (NbFeB), though other magnetic materials may be used. The secondary magnets 40 may be encased in the secondary magnet holder, and in implementations the secondary magnetic holder may be a clear plastic tray similar to, and even in some cases formed of the same material as, aligner tray 34. The secondary magnets 40 could be covered with a white or tooth-colored coating and/or hypoallergenic coatings as well, similar to the magnetizable elements 25, as described above.

Figure 8:
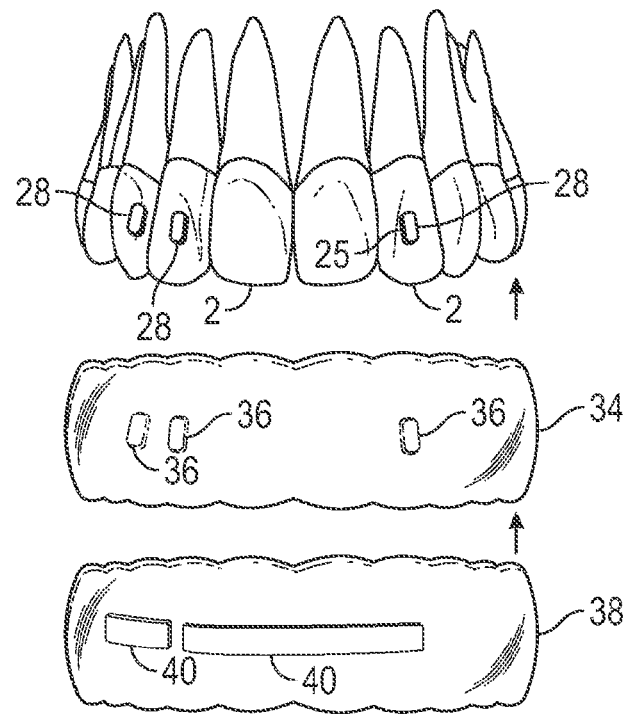
FIG. 8 is a front exploded view of an implementation of a magnetic tooth alignment device for an upper row of teeth.
Figure 9:
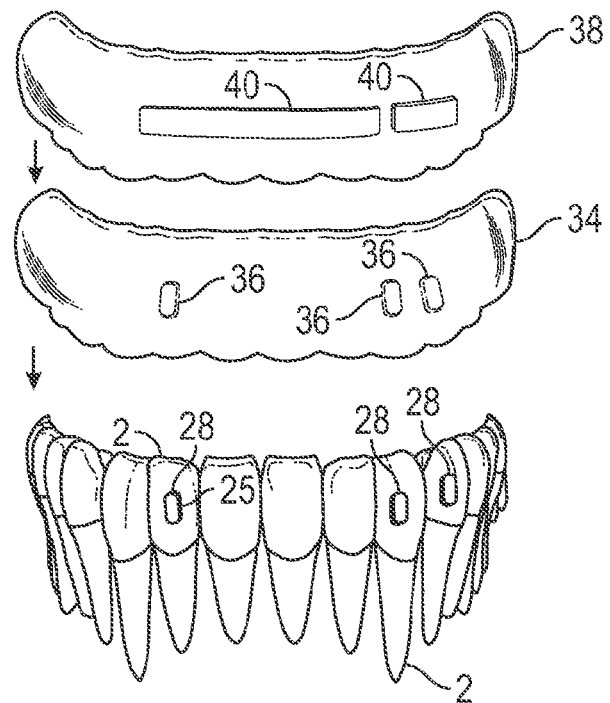
FIG. 9 is a front exploded view of an implementation of a magnetic tooth alignment device for a bottom row of teeth.

FIG. 8 shows an exploded view of a device 24 for use with an upper row of teeth 2. The aligner tray 34 has a plurality of protrusions 36 that are positioned to line up with magnetizable elements 25 so that a cavity 37 is formed between the aligner tray and the magnetizable elements when the aligner tray is encased over the plurality of teeth. Although FIG. 8 numbers the magnetizable elements as first primary magnets 28, it is to be understood, as described herein, that the magnetizable elements in some implementations are not magnets, but are stainless steel or formed of some other metal or magnetizable element that is not independently magnetic. The secondary magnet holder 38 is shown, which generally has a shape substantially similar to that of the aligner tray (though different in some regards, as it is larger, to be able to fit over the aligner tray 34, and as it may not have protrusions as the aligner tray does). The secondary magnet holder 38 is seen with a number of secondary magnets 40 encased therein. In use the aligner tray 34 is "clipped" into place or otherwise slid over the row of teeth so that it is held in place using a friction fit, and the secondary magnet holder 38 is then also clipped or slid in place over the aligner tray 34 so that it also is held in place using a friction fit. The device 24 of FIG. 9 has similar elements and is used in a similar fashion, but is designed for a bottom row of teeth. The arrows in FIGS. 8-9 represent the movement of the elements together to assemble device 24 on either the top row of teeth or bottom row of teeth, respectively.

Figure 10:
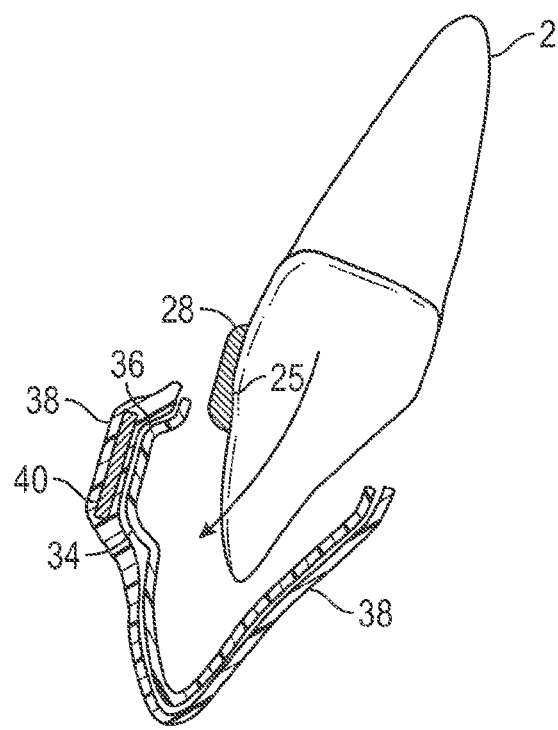
FIG. 10 is a side cross-section view representatively illustrating extrusion of a tooth using an implementation of a magnetic tooth alignment device.
Figure 11:
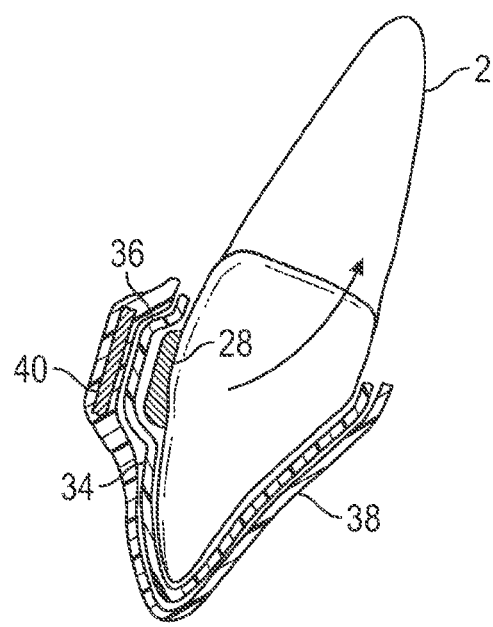
FIG. 11 is a side cross-section view representatively illustrating intrusion of a tooth using an implementation of a magnetic tooth alignment device.
Figure 12:
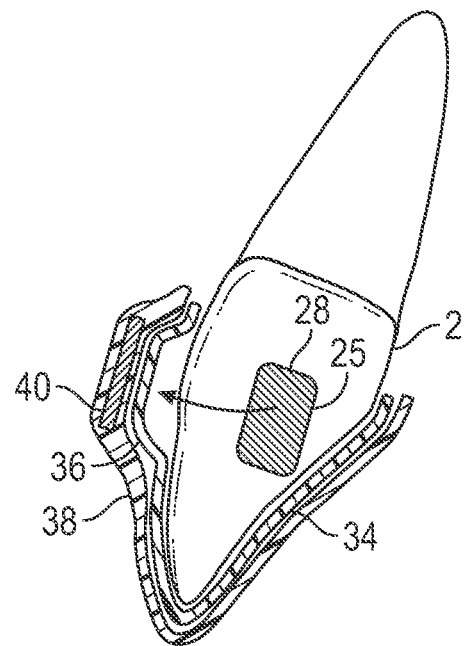
FIG. 12 is a side cross-section view representatively illustrating rotation of a tooth using an implementation of a magnetic tooth alignment device.

FIGS. 10-14 representatively illustrate different types of tooth movement that may be effectuated using a device 4 or 24. In FIG. 10 tooth extrusion is representatively illustrated. The magnetizable element 25 in this case may be either a magnet or a non-magnet, such as steel or another metal, and is attracted towards the secondary magnet 40, thus pulling the tooth downwards. In FIG. 11 tooth intrusion is representatively illustrated. The magnetizable element 25 in this case must be a magnet, and the poles of magnetizable element 25 and secondary magnet 40 are aligned so that the two repel one another, thus pushing the tooth upwards. In FIG. 12 tooth rotation is representatively illustrated. The magnetizable element 25 in this case could be either a non-magnet or a magnet. It is attracted towards the secondary magnet 40 and is thus used to twist or rotate the tooth to a proper position. As may be envisioned, in this case a secondary magnet could be used as the lingual side as well, and magnetizable element 25 could be a magnet, with the elements oriented so that the lingual side secondary magnet repels the magnetizable element and the buccal side secondary magnet attracts it, thus achieving increased rotation. This same concept may be applied to other tooth movements herein wherein one side or portion of a tooth is repelled in this way and another side or portion is attracted, to increase or maximize force and movement of a tooth.

Figure 13:
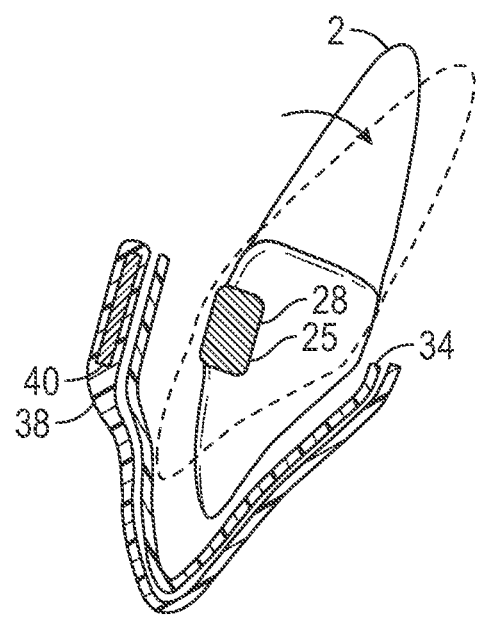
FIG. 13 is a side cross-section view representatively illustrating bodily movement (proclining or reclining) of a tooth using an implementation of a magnetic tooth alignment device.
Figure 14:
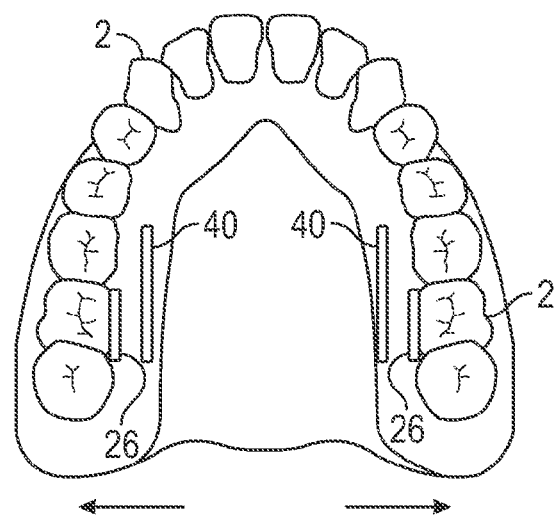
FIG. 14 is a top view representatively illustrating expansion of teeth or a jaw using an implementation of a magnetic tooth alignment device.

FIG. 13 representatively illustrates bodily movement of a tooth (proclining, reclining, or "tipping"). In this case the aligner tray is sized/shaped to allow a tipping movement of the tooth and the dashed outline represents the desired end-position (or intermediate position) of the tooth. The magnetizable element 25 in this case may be either a magnet or a non-magnet, and it is attracted towards the secondary magnet 40. The same movement may be effectuated through repulsion at the lingual side, in which case the magnetizable element would need to be a magnet. FIG. 14 shows a representative example of tooth or jaw expansion achieved using device 4 or 24. The aligner tray and secondary magnet holder are not shown, so that the primary magnets 26 and secondary magnets 40 may be more clearly seen. In this case actual magnets (primary magnets 26) are used so that they can be repelled by secondary magnets 40 by proper alignment of the magnetic poles of each. In each of FIGS. 10-14 the arrows illustrate the projected movement of the tooth or teeth.

When device 24 is used, the aligner tray 34 is configured so that it at least partially encases a plurality of teeth of the patient as well as the magnetizable elements, and the secondary magnet holder 38 is configured so that it at least partially encases the aligner tray 34. In the drawings aligner tray 34 fully encases a plurality of teeth and the secondary magnet holder 38 fully encases the aligner tray 34. Both the aligner tray 34 and the secondary magnet holder 38 may be formed of transparent polymers, and the aligner tray 34, as shown in the drawings, in implementations includes no magnets. The aligner tray 34 may be held to the teeth using only a friction fit and the secondary magnet holder 38 may be held to the aligner tray using only a friction fit, as described. Correspondingly, each may be easily removed and replaced by a user as necessary or as desired.

The magnetizable element may be formed using a powdered metal or magnetic material mixed with an adhesive or it may be a cement magnetic material or cement metallic material. The magnetizable element, when it is a solid element such as a solid metal or magnet element, may be adhered to the tooth using an adhesive which may later be removed using a solvent to remove the magnetizable element.

In places where the description above refers to particular implementations of magnetic tooth alignment devices and related methods and implementing components, sub-components, methods and sub-methods, it should be readily apparent that a number of modifications may be made without departing from the spirit thereof and that these implementations, implementing components, sub-components, methods and sub-methods may be applied to other magnetic tooth alignment devices and related methods.

What is claimed is:

1. A magnetic tooth alignment device, comprising:
a first magnetizable element configured to be adhered to a tooth of a patient;
an aligner tray configured to at least partially encase a plurality of teeth of the patient and the first magnetizable element, and;
a secondary magnet holder configured to at least partially encase the aligner tray, the secondary magnet holder comprising a secondary magnet configured to magnetically interact with the first magnetizable element when the secondary magnet holder is partially encasing the aligner tray;
wherein the secondary magnetic holder is reversibly couplable to the aligner tray.

2. The device of claim 1, wherein the aligner tray is formed of a polymer.

3. The device of claim 1, wherein the aligner tray is transparent.

4. The device of claim 1, wherein the aligner tray includes no magnets.

5. The device of claim 1, wherein the aligner tray is configured to couple with the plurality of teeth of the patient using only a friction fit.

6. The device of claim 1, wherein the aligner tray is configured to fully encase the plurality of teeth of the patient and to fully encase the first magnetizable element.

7. The device of claim 1, wherein the aligner tray comprises a protrusion defining a cavity between the aligner tray and the first magnetizable element.

8. The device of claim 1, wherein the secondary magnet holder is shaped substantially similarly to the aligner tray.

9. The device of claim 1, wherein the secondary magnet holder is configured to couple with the aligner tray using only a friction fit.

10. The device of claim 1, wherein the first magnetizable element is formed of one of a powdered magnetic material mixed with an adhesive and a cement magnetic material.

11. The device of claim 1, wherein an inner wall of the aligner tray is configured to stop movement of the tooth when the first magnetizable element contacts the inner wall of the aligner tray.

12. A magnetic tooth alignment device, comprising:
a first magnetizable element configured to be adhered to a tooth of a patient;
an aligner tray configured to at least partially encase a plurality of teeth of the patient, the aligner tray comprising a protrusion defining a cavity between the aligner tray and the first magnetizable element, the aligner tray comprising no magnets; and;
a secondary magnet holder configured to at least partially encase the aligner tray, the secondary magnet holder comprising a secondary magnet configured to magnetically interact with the first magnetizable element when the secondary magnet holder is partially encasing the aligner tray;
wherein the secondary magnetic holder is reversibly couplable to the aligner tray.

13. The device of claim 12, wherein the secondary magnet holder is configured to couple with the aligner tray using only a friction fit.

14. The device of claim 12, wherein the aligner tray is formed of a polymer.

15. The device of claim 12, wherein the aligner tray is transparent.

16. The device of claim 12, wherein the secondary magnet holder comprises a shape substantially similar to the aligner tray.

17. The device of claim 12, wherein the secondary magnet comprises a dental arch shape.

18. A magnetic tooth alignment device, comprising:
a first magnet configured to be adhered to a tooth of a patient;
an aligner tray configured to at least partially encase a plurality of teeth of the patient and the first magnet, and;
a secondary magnet holder configured to at least partially encase the aligner tray, the secondary magnet holder comprising a secondary magnet configured to magnetically interact with the first magnet when the secondary magnet holder is partially encasing the aligner tray;
wherein the secondary magnetic holder is reversibly couplable to the aligner tray.

19. The device of claim 18, wherein the aligner tray includes no magnets.

20. The device of claim 18, wherein the secondary magnet holder comprises a shape substantially similar to the aligner tray.

* * * * *

UNITED STATES PATENT AND TRADEMARK OFFICE
CERTIFICATE OF CORRECTION

| | | |
|---|---|---|
| PATENT NO. | : 9,775,687 B1 | Page 1 of 1 |
| APPLICATION NO. | : 14/801556 | |
| DATED | : October 3, 2017 | |
| INVENTOR(S) | : Christian Hoybjerg | |

It is certified that error appears in the above-identified patent and that said Letters Patent is hereby corrected as shown below:

On the Title Page

(12) United States Patent, delete "Hoyberg" and insert --Hoybjerg--.

(71) Applicant, delete "Hoyberg" and insert --Hoybjerg--.

(72) Inventor, delete "Hoyberg" and insert --Hoybjerg--.

Signed and Sealed this
Twenty-eighth Day of November, 2017

Joseph Matal
*Performing the Functions and Duties of the*
*Under Secretary of Commerce for Intellectual Property and*
*Director of the United States Patent and Trademark Office*